United States Patent [19]

Hess

[11] Patent Number: 4,927,413
[45] Date of Patent: * May 22, 1990

[54] CATHETER FOR BALLOON ANGIOPLASTY
[75] Inventor: Robert Hess, Portola Valley, Calif.
[73] Assignee: Progressive Angioplasty Systems, Inc., Menlo Park, Calif.
[ * ] Notice: The portion of the term of this patent subsequent to Feb. 28, 2006 has been disclaimed.
[21] Appl. No.: 299,149
[22] PCT Filed: Aug. 24, 1988
[86] PCT No.: PCT/US88/02826
§ 371 Date: Nov. 21, 1988
§ 102(e) Date: Nov. 21, 1988

Related U.S. Application Data
[63] Continuation-in-part of Ser. No. 88,264, Aug. 24, 1987, Pat. No. 4,808,164.
[51] Int. Cl.⁵ ............................................. A61M 25/00
[52] U.S. Cl. ........................................ 604/95; 604/96; 604/170; 606/194; 606/7
[58] Field of Search ............. 128/344, 348.1, 656-658, 128/772; 604/95, 96, 170, 194

[56] References Cited

U.S. PATENT DOCUMENTS

| | | | |
|---|---|---|---|
| 3,435,824 | 4/1969 | Gamponia | 128/334 |
| 3,618,614 | 11/1971 | Flynn | 128/348 |
| 3,720,210 | 3/1973 | Diettrich | 128/214.4 |
| 3,757,768 | 9/1973 | Kline | 128/2 M |
| 3,871,358 | 3/1975 | Fukuda et al. | 128/2 M |
| 4,033,331 | 7/1977 | Guss et al. | 128/2 M |
| 4,276,874 | 7/1981 | Wolvek et al. | 128/1 D |
| 4,285,341 | 8/1981 | Pollack | 128/214 R |
| 4,301,797 | 11/1981 | Pollack | 128/214 R |
| 4,323,071 | 4/1982 | Simpson et al. | 128/343 |
| 4,351,341 | 9/1982 | Goldberg | 128/348 |
| 4,411,055 | 10/1983 | Simpson et al. | 29/447 |
| 4,445,892 | 5/1984 | Hussein et al. | 604/101 |
| 4,448,188 | 5/1984 | Loeb | 128/6 |
| 4,449,528 | 5/1984 | Auth et al. | 128/303.1 |
| 4,456,017 | 6/1984 | Miles | 128/772 |
| 4,538,622 | 9/1985 | Samson et al. | 128/772 |
| 4,545,390 | 10/1985 | Leary | 128/772 |
| 4,548,206 | 10/1985 | Osborne | 128/772 |
| 4,573,470 | 3/1986 | Samson et al. | 128/344 |
| 4,582,181 | 4/1986 | Samson | 128/348.1 |
| 4,616,653 | 10/1986 | Samson et al. | 128/344 |
| 4,619,274 | 10/1986 | Morrison | 128/772 |
| 4,641,654 | 2/1987 | Samson et al. | 128/344 |
| 4,643,186 | 2/1987 | Rosen et al. | 128/303.1 |
| 4,654,024 | 3/1987 | Crittenden et al. | 604/49 |
| 4,662,368 | 5/1987 | Hussein et al. | 128/303.1 |
| 4,669,465 | 6/1987 | Moore et al. | 128/303.1 |
| 4,672,961 | 6/1987 | Davies | 128/303.1 |
| 4,672,962 | 6/1987 | Hershenson | 128/303.1 |
| 4,676,249 | 6/1987 | Arenas et al. | 128/657 |
| 4,679,557 | 7/1987 | Opie et al. | 128/305 |
| 4,686,982 | 8/1987 | Nash | 128/305 |
| 4,719,924 | 1/1988 | Crittenden et al. | 128/772 |
| 4,721,117 | 1/1988 | Mar et al. | 128/772 |
| 4,723,936 | 2/1988 | Buchbinder et al. | 604/95 |
| 4,728,319 | 3/1988 | Masch | 604/22 |
| 4,729,763 | 3/1988 | Henrie | 604/22 |
| 4,808,164 | 2/1989 | Hess | 128/344 X |
| 4,830,023 | 5/1989 | Toledo et al. | 128/772 |

FOREIGN PATENT DOCUMENTS 0176865 4/1986 European Pat. Off. .
WO/00844 2/1988 World Int. Prop. O. ............ 604/96

Primary Examiner—Dalton L. Truluck
Attorney, Agent, or Firm—Burns, Doane, Swecker & Mathis

[57] ABSTRACT

A catheter for balloon angioplasty includes a flexible shaft (12) defining a hollow passage (18), the shaft having first (14) and second (16) ends. A core means (20) is movably and removably mounted within the hollow passage, the core means having first and second ends adjacent the first and second ends of the shaft. The core means has a first flexible portion (26) adjacent the first end and a second flexible portion (28) of greater flexibility adjacent the second end. The core means may also have an enlarged terminal knob (30) at the second end. A flexible guide wire (32) may be fixed to the second end of either the shaft or the core means. The catheter may be inserted into a vascular tree. After removal of the core means, the core means may be replaced by an exchange wire, an angioscope, a laser fiber, or a rotatable wire. Also, when the core means is replaced by an exchange wire, the shaft may then be removed and replaced by either a different balloon angioplasty catheter or a perfusion catheter.

10 Claims, 3 Drawing Sheets

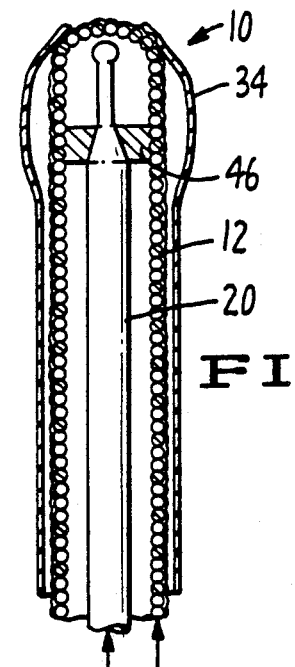
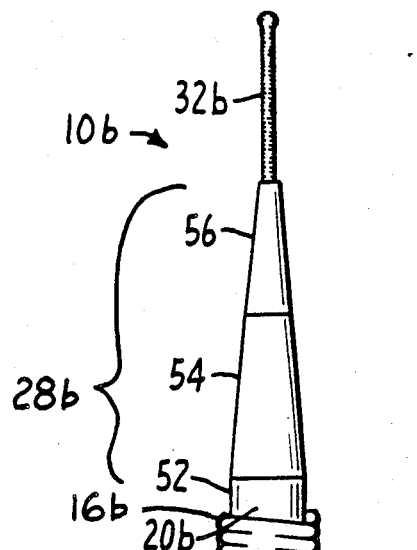

CATHETER FOR BALLOON ANGIOPLASTY

This application is a continuation-in-part of U.S. patent application Ser. No. 088,264 filed Aug. 24, 1987 now U.S. Pat. No. 4,808,164.

BACKGROUND OF THE INVENTION

1. Field of the Invention

This invention relates generally to surgical procedures employing a flexible catheter guide and more particularly to an apparatus for use in balloon angioplasty.

2. Prior Art

Catheters require the capability of being pushed and flexibility in order to be effectively inserted into blood vessels and maneuvered through a vascular tree. Often a hollow spring wire shaft is used as a catheter, such catheter including a movable core wire.

A balloon may be used in conjunction with various catheter constructions such that the balloon may be inflated within the vessel, thereby opening blockages found therein. However, the combination of a hollow spring wire shaft and a movable core wire of variable properties has not been used in conjunction with a balloon.

U.S. Pat. No. 4,276,874 discusses a balloon catheter including an elongated coil spring defining an inner passage, the spring being covered by silicone in the form of an extendable sheath, strain collar, and a balloon tip affixed to the strain relief collar. A portion of the elongated coil spring and sheath form a support structure which perceptibly elongates when excessive stretching force is applied to the support structure when moving the balloon through a body passage. Unfortunately, such a catheter is unsteerable and does not have variable flexibility.

Another device, disclosed in U.S. Pat. No. 4,723,936, is a coil spring guide including a deflectable tip which comprises a coil spring covered by a sheath, a core wire within the coil spring extending the length of the coil spring, and a head member. At the proximal end of the coil spring guide a mechanism is provided to enable movement of the coil spring relative to the core wire. The core wire is eccentrically fixed to the back side of the head member and adjacent a lateral side thereof, thereby causing compression of the distal and spring coils and deflection thereof in a direction laterally from the side of the head member to which the core extension is fixed upon rearward movement of the core wire. Such a standard low profile catheter with a fixed wire system additionally does not offer a combined over-the-wire system nor variable column strength.

Still another device, disclosed in U.S. Pat. No. 4,548,206, is directed to a catheter wire guide with a movable mandrel having a tapered tip which permits the flexibility of the distal tip of the wire guide to be varied. This device provides for a helically wound wire having an opening therethrough and a mandrel positioned within the opening and longitudinally movable therein relative to the helically wound wire for varying the flexibility of the distal tip of the wire guide. The device is a diagnostic or wire placement device and not a balloon catheter suitable for angioplasty.

Although the foregoing devices include some advantageous features, they are limited in that they do not combine the following desirable features: a movable core means; variable stiffness of the shaft secondary to the movable core means and therefore variable trackability and pushability; a deflection mechanism for deflecting the tip of the catheter while still allowing torque and rotation; an ultra low profile, such that the device may be used in conjunction with a standard diagnostic coronary catheter rather than a guide catheter, referred to as a PTCA guiding catheter; the capability to transform from a fixed wire system to an over-the-wire system by removal of the movable core means; and the ability to insert either fiber optic angioscopes or laser fibers through the hollow portion of the catheter.

The foregoing illustrates limitations known to exist in present devices. Thus, it is apparent that it would be advantageous to provide an alternative device directed to overcoming one or more of the limitations set forth above. Accordingly, a suitable alternative is herein provided including features more fully disclosed hereinafter.

SUMMARY OF THE INVENTION

One aspect of the present invention provides a catheter for balloon angioplasty comprising:

a flexible shaft having a hollow passage therein, said flexible shaft having a first proximal end which is open and a second distal end which is closed;

a core means movably and removably mounted within said passage, said core means having a first proximal end and a second distal end, said ends adjacent said first and second ends of said flexible shaft, respectively, said core means having a first flexible portion extending along its length from said first proximal end and a second flexible portion being of greater flexibility than said first flexible portion, said second flexible portion extending to said second distal end, said core means having an enlarged terminal knob at said second distal end thereof, said knob contacting said second distal end of said flexible shaft upon axial movement of said core means, further axial movement of said core means causing bending and buckling of said second flexible portion of said core means in turn bending said flexible shaft and causing angulation of said second distal end of said flexible shaft;

a flexible guide wire externally attached to the second distal end of said flexible shaft, said flexible guide wire axially extending away from said second distal end; and an inflatable member having a non-inflatable sheath covering an external surface of said flexible shaft near the second distal end of said flexible shaft and further including means for inflating said inflatable member.

Another aspect of the instant invention provides a catheter for balloon angioplasty comprising:

a flexible shaft having a hollow passage therein, said flexible shaft having a first proximal end which is open and a second distal end which is partially open having a reduced cross-section;

a core means movably and removably mounted within said passage, said core means having a first proximal end and a second distal end, said ends adjacent said first and second ends of said flexible shaft, respectively, said core means having a first flexible portion extending along its length from said first proximal end and a second flexible portion being of greater flexibility than said first flexible portion, said second flexible portion extending to said second proximal end, said core means having an enlarged terminal knob at said second distal end thereof, said knob contacting said reduced cross-section of said second distal end of said flexible shaft upon axial movement of said core means, further axial movement of said core means causing bending and buckling of said second flexible portion of said core means bending said flexible shaft and causing angulation of said second distal end of said flexible shaft; and a flexible guide wire attached to said terminal knob and axially extending away from said knob, said guide wire axially extensible through the opening in said second distal end of said flexible shaft.

Yet another aspect of the instant invention provides a catheter for balloon angioplasty comprising:

a flexible shaft having a sealed hollow passage defined therein and having a first proximal end and a second distal end, both said ends being open;

a core means movably, removably and substantially contained within said flexible shaft, said core means having a first proximate end and a second distal end and having a first flexible portion extending from said first proximate end and a second flexible portion terminating in said second distal end of said core means, said second flexible portion being of greater flexibility than said first flexible portion, said second flexible portion having a variable core strength along the length thereof from greater to lesser strength extending toward the second distal end of said core means to provide trackability, pushability and flexibility of said catheter;

a flexible guide wire fixed to and further axially extending from the second distal end of said core means; and an inflatable member having a non-inflatable sheath covering an external surface of said flexible shaft near the second distal end of said flexible shaft and further including means for inflating said inflatable member.

Further aspects of the invention reside in the methods of using the catheters of the present invention and in providing a kit containing the catheters and other components sized to be used in conjunction with said catheters.

The foregoing and other aspects will become apparent from the following detailed description of the invention when considered in conjunction with the accompanying drawing. It is to be expressly understood, however, that the drawing is not intended as a definition of the invention but is for the purpose of illustration only.

BRIEF DESCRIPTION OF THE DRAWING

FIG. 5 is a cross-sectional view illustrating a third embodiment of the invention including a power source;

FIG. 6 is a cross-sectional view illustrating a fourth embodiment of the invention;

FIG. 7 is a cross-sectional view of a fifth embodiment of the invention; and

DETAILED DESCRIPTION

Figure 1:
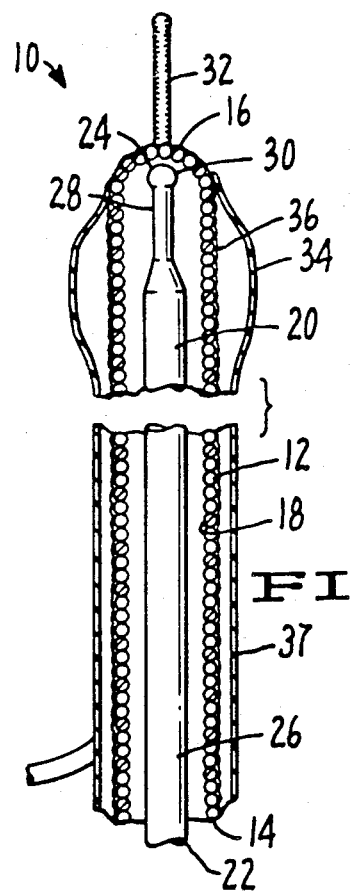
FIG. 1 is a cross-sectional view illustrating a portion of a first embodiment of the catheter of the invention.

A catheter for balloon angioplasty, generally designed 10, and illustrated in FIG. 1, includes a flexible shaft 12 preferably formed of a suitable metal such as Type 304 Stainless Steel and having an outside diameter of from about 0.014 to about 0.035 inch (0.35 mm to about 0.88 mm). Shaft 12 has an open first or proximal end 14, a closed second or distal end 16, and defines a hollow passage 18 therein.

A flexible core means 20, preferably formed of a suitable metal such as Type 304 Stainless Steel has a diameter of from about 0.008 to 0.030 inch (0.20 mm to about 0.75 mm). Core means 20 is movably and removably mounted within passage 18 and includes a first proximal end 22 and a second distal end 24 adjacent first and second ends 14, 16, respectively, of shaft 12. Core means 20 has a first portion 26 (extending from first end 22) which has a first flexibility and a second portion 28 (adjacent and terminating at second end 24) which is tapered to a smaller diameter than first portion 26 to provide a second flexibility, said second flexibility being greater than the aforesaid first flexibility. Core means 20 also includes an enlarged terminal knob 30 formed at second end 24.

A flexible guide wire 32, preferably formed of a suitable metal such as platinum to provide radiopacity and having a diameter of from about 0.008 to about 0.018 inch (0.20 mm to about 0.45 mm), may be fixed securely by suitable means such as adhesives, welding or brazing, to second end 16 of shaft 12. Guide wire 32 is of a greater flexibility than the aforesaid second flexibility.

An inflatable member such as an angioplasty balloon 34 of polymeric material is attached or affixed to second end 16 of shaft 12 to substantially cover an external surface 36 of shaft 12 in such a manner that second end 16 of shaft 12 and guide wire 32 are free of such covering. Such angioplasty balloons are well-known in the art and can be formed in one piece along with a non-inflatable sheath or as a separate component and attached to non-inflatable shaft. A separate component may allow the use of dissimilar materials between the non-inflatable sheath and the balloon. As seen in FIGS. 1, 2 and 4–7 the balloons 34, 34a and 34b are formed as a one-piece component with non-inflatable sheath 37, 37a and 37b. It is understood that shaft 12 is sealed with respect to passage 18, such as by use of a plastic covering, so that balloon 34 may be inflated. A suitable inflation means 38 (see FIG. 2) may be connected via conduit 40 to inflate balloon 34. A finger loop 42 is suitably connected to shaft 12, and a corresponding finger loop 44 is similarly connected to core means 20. This feature is desirable in that it allows variable column strength of shaft 12 and variable flexibility which is controlled by the operator by either advancing or withdrawing movable core means 20. If stiffness of the shaft is required to push through tight lesions, core means 20 is advanced, and the entire catheter 10 becomes stiffer and has greater ability to be pushed. If extreme flexibility is required, as may be the case in navigating through extremely tortuous vessels, the core means 20 of catheter 10 may be withdrawn; see FIG. 3. Core means 20 may be withdrawn partially or totally, thereby increasing the flexibility of catheter 10 from the distal portion to the proximal portion, depending upon how far movable core means 20 is withdrawn. Because shaft 12 of catheter 10 consists of spring wire rather than polymers, shaft 12, even without core means 20, has a fair degree of column strength, yet has extreme flexibility. During any given angioplasty procedure, either extreme flexibility or column strength, or both, may be required; therefore, during any procedure, core means 20 may be pulled back and advanced according to the desires of the operator. As an additional feature, core means 20 may be replaced with a second core means of greater or lesser flexibility. Thus, a "fin-tuning" of column strength is available to the operator.

A modification (third embodiment) of the shaft of FIG. 1 is illustrated in FIG. 5 and includes a ferrite material 46 provided within shaft 12. Means 48 provides a radio frequency signal to be received by ferrite material 46 using shaft 12 and core means 20 as conductors, thus heating catheter 10. Alternatively, another modification (fourth embodiment) is illustrated in FIG. 6 and may include the ferrite material 46a impregnated within a portion of the inflatable member 34a. Similarly, means 48 provides the aforesaid radio frequency signal to be received by ferrite material 46a.

Figure 4:
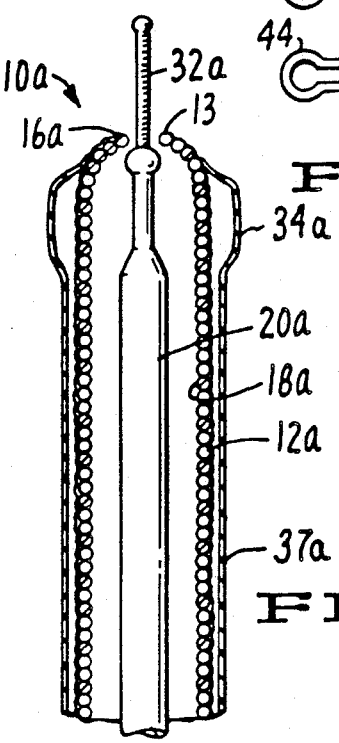
FIG. 4 is a cross-sectional view illustrating a second embodiment of the invention.

Another modification (second embodiment) of the shaft is illustrated in FIG. 4 wherein shaft 12a includes an aperture 13 formed in second end 16a. Core means 20a is also modified in that flexible guide wire 32a is fixedly attached to knob 30a. Balloon 34a and finger loops 42, 44 (described above in connection with shaft 12 and core means 20 illustrated in FIG. 2) may also be associated with the combination of shaft 12a and core means 20a of FIG. 4.

The unique construction of catheter 10 (FIG. 1) and catheter 10a (FIG. 4) allows for both tip deflection and torquing of leading guide wire 32. In the first, the shaft 12 of catheter 10 is closed at the distal end. As core means 20 pushes axially forward and is advanced into contact with closed end 16, catheter 10 is deflected. This deflection is a result of the fact that core means 20 is more flexible in portion 28 than in portion 26. This increased flexibility of the distal portion of core means 20 (as opposed to the proximal portion) is the result of either tapering core means 20 so that it is thinner distally than proximally, or by creating a joint therein such that an elbow effect is created at the joint—when the catheter is pushed forward, the elbow bends deflecting the end 24 of core means 20 and the end 16 of shaft 12 as well, because shaft 12 is a flexible spring wire. The greater the force applied to core means 20, the greater the extent of angulation of catheter 10. The radius of angulation of catheter 10 is controlled by the location of the taper or by the position of the elbow joint. The closer the elbow joint to end 24, or the shorter the taper at end 24, the smaller the radius of angulation and vice versa. Angulation of greater than 120° can be obtained using these criteria.

The end of core means 20 is blunted by terminal knob 30 in order to provide a large surface bearing area between the core means 20 and the closed end 16. In FIG. 1, a very flexible guide wire 32 of about 1–7 cm in length and 0.20 mm to about 0.45 mm in diameter may be fixedly connected to end 16 of shaft 12. This "fixed wire", as connected to the distal portion of shaft 12, allows the entire catheter 10 to be advanced through the arteries with minimal trauma. Guide wire 32 can be deflected by deflecting end 16 of shaft 12 and can be torqued by torquing shaft 12 of catheter 10.

The similar but slightly modified and steerable catheter 10a is illustrated in FIG. 4. In this variation, distal end 16a of shaft 12a is not entirely closed but includes aperture 13. Core means 20a is similar to core means 20, except that the highly flexible terminal guide wire 32 is preferably welded to knob 30a. In this system, core means 20a is withdrawn or advanced to vary the shaft stiffness, as explained above. The main difference between the variations is that flexible guide wire 32 is connected directly to the core means, rather than to the shaft. As core means 20a is advanced, guide wire 32 advances so that it protrudes through aperture 13 in end 16a of shaft 12a. However, the diameter of knob 30a is larger than the diameter of aperture 13 at the position of the weld between guide wire 32 and core means 20a. Therefore, in order to deflect catheter 10a, the operator axially advances core means 20a so that knob 30a pushes against the distal end 16a of shaft 12a. In this manner, the core means is deflected due to the taper in core means 20a. This deflects both shaft 12a of catheter 10a and guide wire 32 which protrudes from end 16a. Further, if the operator requires torque on guide wire 32, the operator rotates the proximal portion of core means 20a thereby transmitting the torque through core means 20a to the distal guide wire 32, and thus torquing the guide wire. Therefore, this system allows the operator to have both tip angulation and the ability to torque through an ultra low profile system with variable shaft flexibility.

FIG. 7 illustrates a fifth embodiment of the invention, shown generally at 10b, having a movable and removable core means 20 of variable strength, as will be discussed further. Core means 20b is contained within flexible shaft 12b having a second distal end 16b. Flexible shaft 12b is preferably a coated wire wound member (see coating 50), which preferably constitutes an inner lumen surrounded by balloon 34b of polymeric material. Guide wire 32b extends from the end of core means 20b. Core means 20b is described as having variable core strength because, similar to the earlier-described embodiments, it has a first flexible portion 26b extending from the first proximate end of the core means 20b and a second flexible portion 28b terminating in the second distal end of the core means 20b. Second flexible portion 28b preferably comprises a series of tapered cross-sections 52, 54 and 56 of different diameter, thereby exhibiting a variable strength when subjected to bending. These cross-sections may be tapered, as shown, or varied by using progressively smaller uniform cross-sections connected to each other in a stepped fashion. Other equivalent structures are within the scope of the invention. It can be seen that the axial position of the core means 20b relative to the second distal end of the flexible shaft 12b will determine the over-all trackability, pushability, flexibility and steerability of the distal end of the catheter. The further the second flexible portion 28b (tapered cross-sections 52, 54 and 56) of core means 20b extends beyond second distal end 16b of the shaft 12b, the larger the cross-section of the core means in the vicinity of balloon 34b and therefore the greater the stiffness of the distal end of the catheter. The flexibility of the distal end of the catheter is determined by a lesser cross-section in the vicinity of balloon 34b which is accomplished by retraction of the second flexible portion 28b with respect to second distal end 16b. Movement of said second flexible portion 28b of said core means axially relative to said second distal end 16b of said flexible shaft again determines the flexibility, pushability, trackability and steerability of the catheter. Extension of the second flexible portion 28b relative to the second distal end 16b of said flexible shaft increases pushability of the catheter and decreases flexibility and trackability, retraction of the second flexible portion 28b from such extended position increasing flexibility and trackability of the catheter with an accompanying decrease in pushability.

Because catheter 10 is constructed with a movable core means 20, shaft 12 becomes hollow when core means 20 is removed. In FIG. 4, aperture 13 (in end 16a of shaft 12a) can be used in several settings. This also applies to FIG. 7. If the operator proceeding with this system comes upon an unexpected closure of the artery necessitating the insertion of a long exchange wire so that a "bail out" catheter may be placed or a larger or smaller balloon can be inserted, then the operator may remove core means 20a of catheter 10a and insert a long exchange wire through the hollow passage 18a of shaft 12a, the long exchange wire protruding through aperture 13 in end 16a of shaft 12a; due to the absence of knob 30a, shaft 12a may be removed, and a larger or smaller balloon or "bail-out" catheter may be placed over it. This is a unique feature of this system in that no other angulating, torquable catheter is able to provide the capabilities of both a fixed wire and an over-the-wire system in the same catheter.

It can be seen that all of the above also applies to the structure of FIG. 4 and FIG. 7 wherein like components have like reference numerals. For the purpose of the following discussion, it is understood that the embodiments of FIGS. 4 and 7 are both open at their distal ends and allow some similar procedures. For the sake of illustration, some attempt will be made in describing both embodiments by referring to the reference numerals in both FIGS. 4 and 7.

The new procedures of coronary angioscopy and laser angioplasty may have significant use as adjuncts to balloon angioplasty. The catheter of this invention has significant applicability to both angioscopy and laser angioplasty. If the operator is using catheter 10a of FIG. 4 (or 10b of FIG. 7) and then decides to perform coronary angioscopy, the following steps can be undertaken. First, catheter 10a (or catheter 10b) is advanced to the location of interest using the standard technique. Second, core means 20a (or core means 20b) of catheter 10a (or catheter 10b) is withdrawn, and the operator then inserts an appropriately-sized, highly-flexible angioscope into the shaft of the catheter and advances it to aperture 13. Therefore, this system uniquely provides the ability to perform coronary angioscopy during balloon angioplasty. By advancing the coronary angioscope through hollow passage 18a, the angioscope can be advanced without its actually coming into contact with the arterial wall. That is, the angioscope is always enclosed while within the shaft 12a (or shaft 12b) of catheter 10a (or catheter 10b). This is a significant improvement over current methods of coronary angioscopy which expose the tip of the angioscope to the wall of the artery, thereby allowing the potential for abrasion and dissection of the arterial wall. Another hazard of current methods is of protrusion of the sharp tip of the angioscope through the plastic at bend regions. The metallic structure of catheter 10a (or catheter 10b) prevents the protrusion from occurring in this system. The flushing of blood may then be performed through the guiding catheter (with or without the balloon inflated) to allow a clear field in which to view with the angioscope.

Similarly, if laser angioplasty is performed, the laser fiber (connected to virtually any laser source) can be advanced through hollow passage 18a of catheter 10a up to and, if necessary, protruding through aperture 13. This, again, allows advancement of the laser fiber without contacting the arterial wall, thus minimizing the potential for abrasion. This function is not easily performed with conventional polymer catheters since the tip of the laser fiber can be quite sharp and may protrude through the plastic at bend regions. The metallic structure of catheter 10a (or catheter 10b) prevents protrusion with this system.

Figure 8:
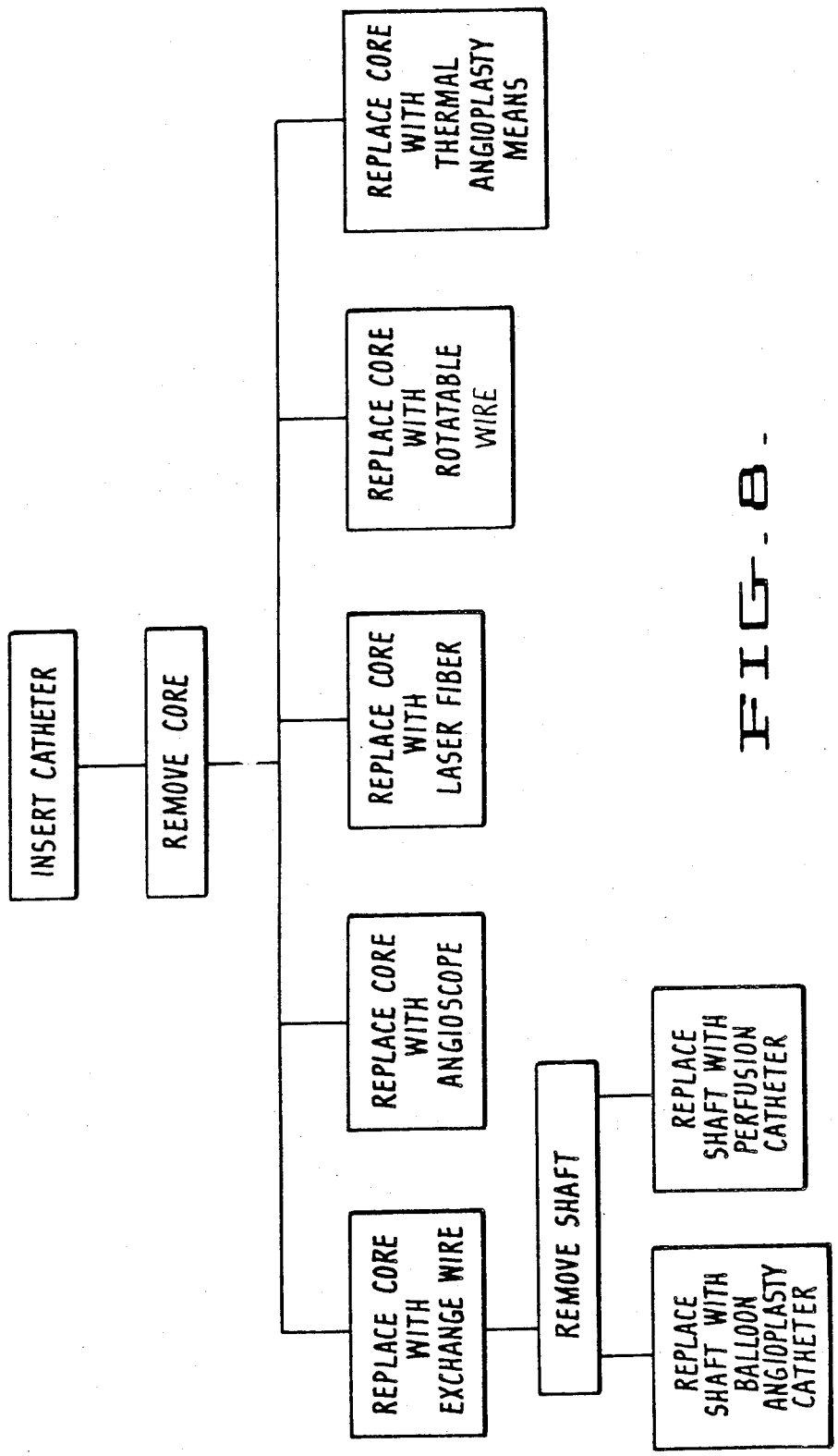
FIG. 8 is a schematic view of a flow diagram of methods of using the present invention.

FIG. 8 shows a schematic flow diagram of alternative methods using other well-known components sized to fit, with respect to the catheters of the sized to fit, with respect to the catheters of the instant invention, in surgical techniques. These components will continue to be described.

Figure 2:
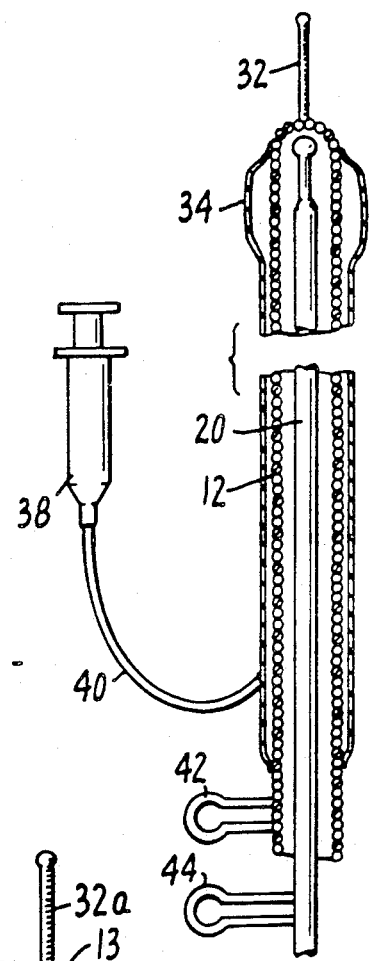
FIG. 2 is a second cross-sectional view illustrating the entire first embodiment of FIG. 1 of the invention.
Figure 3:
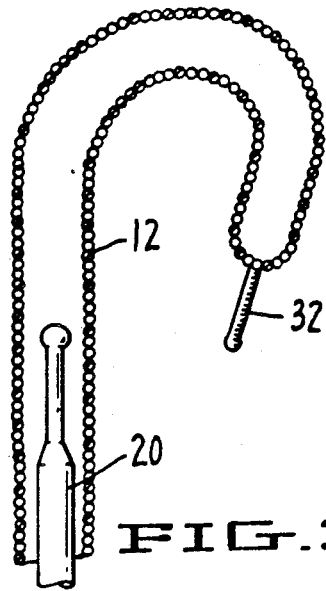
FIG. 3 is a third cross-sectional view illustrating the first embodiment of FIG. 1 of the invention without an inflatable member and showing the core means withdrawn from the shaft.

Balloon 34a (or balloon 34b) is placed directly over shaft 12a (or shaft 12b) in this balloon angioplasty system. Balloon 34a (or balloon 34b) is constructed of polymer, the polymer being connected and attached or affixed to distal end 16a (or end 16b) of shaft 12a (or shaft 12b). Balloon 34a (or balloon 34b) is somewhat proximal to end 16a (or end 16b); then the polymer extends back to the proximal portion of catheter 10a (or catheter 10b). The proximal portion of balloon 34a (or balloon 34b) is connected to the balloon inflation apparatus, as shown in FIG. 2. Balloon 34a (or balloon 34b) can be composed of any one of a variety of standard materials (polyethylene, polyvinylchloride) or may be made of new ultra-thin materials, such as the DuPont product PET. Since balloon 34a (or balloon 34b) is placed directly over shaft 12a (or shaft 12b) and the balloon material can be very low profile, this catheter has an extremely low profile, only slightly above that of shaft 12a (or shaft 12b). Shaft 12a (or shaft 12b) can have a variable size (depending upon what is desired) and can range from about 0.014 inch (0.35 mm) to any upper size desired. The incorporation of novel polymer technology is also possible. In this system, some catheters could be composed of available polymers and strengthened with thin strands of impregnated fibers. This would allow very high burst strengths (in excess of 15 atmospheres) yet not create a high profile. This would allow for high pressure inflations with a very low profile catheter system. catheters rather than the special PTCA guide catheters currently used in all angioplasty procedures. The diagnostic catheters have handling characteristics superior to the PTCA guide catheters and are also smaller in diameter and less traumatic to the coronary arteries. The use of diagnostic catheters, therefore, provides a significant advantage over available systems.

The optionally provided pistol grip handles provided by loops 42, 44 connected to the proximal portion of shaft 12, 12a and core means 20, 20a allow very fine control of the core means and the shaft and manipulation by only one hand (FIG. 2). This, therefore, provides significant advantages over currently available systems. The pistol grip handles allow simple advancement or withdrawal of the entire catheter system; individual advancement or withdrawal of the core means and shaft; torque of the shaft, the core means, or both; advancement or withdrawal of the core means to vary shaft flexibility and the shaft's ability to be pushed; and core means advancement so that tip angulation can be achieved through the mechanisms described above. This is a significant advantage over currently available systems.

A modified version of catheter 10a could also be useful in balloon valvuplasty. The modifications would incorporate a larger balloon (3–8 cm in length, 12–25 mm in diameter). Shaft 12a of FIG. 4 would be employed. These modifications would allow tip steerability for retrograde crossing of the aortic valve (no current valvuplasty system has steerability), and a movable core means for variable flexibility and column strength. (Great flexibility is required for navigating up tortuous, peripheral vessels to reach the valve, yet column strength is required to move across the narrowed valve orifice). Once the valve is crossed, the core means can be removed, allowing pressure monitoring through the hollow shaft. (Distal pressure monitoring during valvuplasty is not possible with conventional systems, and the spring wire is sufficiently flexible and atraumatic to sit in the ventricle without the core means and tip wire). The low profile of the shaft with its fiber-strengthened balloon allows for an over-all low profile.

A significant modification can be achieved using catheter 10 or 10a, or virtually any conventional balloon angioplasty catheter. There is scientific evidence to support the notion that heating the artery to a temperature greater than some critical temperature, currently thought to be about 70° C., may ameliorate the restenosis found in 25-30% of patients following balloon angioplasty. Restenosis is considered to be the single most significant complication of balloon angioplasty, and any device which could ameliorate this complication would have enormous clinical impact. Several potential solutions to this problem are proposed; all are related to methods of heating the balloon. One solution (FIG. 5) involves placing a small amount of ferrite material 46 at the distal end of core means 20 in the balloon portion of catheter 10. This ferrite material is ferromagnetic and is capable of being heated when coupled to an appropriately tuned radio frequency energy source. Radio frequency energy in the megahertz or microwave portion of the electromagnetic spectrum is transmitted down shaft 12 of angioplasty catheter 10 using core means 20 and shaft 12 as conducting material. This energy then couples to the ferrite material 46 and generates intense localized heating. Heat from ferrite material 46 heats the fluid used to inflate balloon 34, providing a balloon heated to greater than 70° C. This balloon could be used for coronary or peripheral arterial inflation, and by virtue of the temperature achieved is capable of killing smooth muscle cells in the wall of the artery. These smooth muscle cells are responsible for restenosis following angioplasty and it is claimed that the thermal energy from the balloon catheter would kill the progenitor cells responsible for restenosis. Another solution (FIG. 6) involves the impregnation of the balloon material itself with the ferromagnetic material 46. The radio frequency energy is then delivered from outside the body and is coupled into the ferromagnetic material 46 in balloon 34. That is, the ferromagnetic material in balloon 34 acts as an antenna for the radio frequency energy. This generates intense heating (greater than 70° C.) of balloon 34 and kills the smooth muscle cells, thereby preventing restenosis. Other suitable means of heating the balloon will yield equally effective results.

Described above is a system for producing a small central lumen in a totally occluded artery which could then be followed by balloon angioplasty. If an artery is totally occluded it is difficult to place the balloon into the occlusion so that inflation can commence. It is proposed that the above-described catheter 10a can be used to solve this problem. Catheter 10a can be advanced to the blockage. Then core means 20a can be removed, leaving behind the hollow shaft 12a. Through passage 10a in shaft 12a a specially fabricated wire which protrudes through aperture 13 can be placed. The proximal portion of the new central wire is connected to a rotating mechanism which is powered by either batteries or standard electric current. The rotating mechanism rotates from about 10,000 to about 250,000 rpm, thereby causing the central wire to rotate at the same frequency. This rotating wire will act as a drill and burrow a small central channel through the totally occluded artery. Once this has occurred, the catheter is advanced through the blockage such that the balloon is then placed within the blockage, the balloon being capable of dilating the blockage. This procedure can be applied to sequential recanalization and balloon dilation of totally occluded arteries.

Although the present invention has been described with particular reference to the preferred embodiments, such disclosure should not be interpreted as limiting. Other alternatives and modifications will no doubt become apparent to those skilled in the art after having read the preceding disclosure.

What is claimed is:

1. A catheter for balloon angioplasty comprising:
a flexible shaft having a sealed hollow passage defined therein and having a first proximal end and a second distal end, both said ends being open, said flexible shaft being a coated wire wound member, said coating being fluid impervious and extending along substantially the entire length of the wire wound member, the wire wound member being substantially round in cross-section and resistant to flattening in cross-section when said flexible shaft is bent along the length thereof in the tortuous path of a coronary artery, allowing close tolerances for a member that may be inserted therein, the coated wire wound member inherently having high column strength providing pushability while maintaining a high degree of flexibility and being resistant to a preset in overall shape when the catheter is coiled for storage;
a core means movably, removably and substantially contained within said flexible shaft, said core means having a first proximate end and a second distal end and having a first flexible portion extending from said first proximate end and a second flexible portion terminating in said second distal end of said core means, said second flexible portion being of greater flexibility than said first flexible portion, said second flexible portion having a variable core strength along the length thereof from greater to lesser strength extending toward the second distal end of said core means, said second flexible portion being tapered along the length thereof such that essentially all of said second flexible portion can generally be extended within a coronary artery to maximize the variable stiffness of said catheter, the combination of the core means and the coated wire wound member providing variable trackability, pushability and flexibility of said catheter;
a flexible guide wire fixed to and further axially extending from the second distal end of said core means; and
an inflatable member having a non-inflatable sheath covering an external surface of said flexible shaft near the second distal end of said flexible shaft and further including means for inflating said inflatable member.

2. A catheter as in claim 1 wherein said second flexible portion of said core means comprises a series of tapered sections.

3. A kit comprising:
a catheter having a flexible shaft having a sealed hollow passage defined therein and having a first proximal end and a second distal end, both said ends being open, said flexible shaft being a coated wire wound member, said coating being fluid impervious and extending along substantially the entire length of the wire wound member, the wire wound member being substantially round in cross-section and resistant to flattening in cross-section when said flexible shaft is bent along the length thereof in the tortuous path of a coronary artery, allowing close tolerances for a member that may be inserted therein, the coated wire wound member inherently having high column strength providing pushability while maintaining a high degree of flexibility and being resistant to a preset in overall shape when the catheter is coiled for storage, said catheter including a core means movably, removably and substantially contained within said flexible shaft, said core means having a first proximate end and a second distal end and having a first flexible portion extending from said first proximate end and a second flexible portion terminating in said second distal end of said core means, said second flexible portion being of greater flexibility than said first flexible portion, said second flexible portion having a variable core strength along the length thereof from greater to lesser strength extending toward the second distal end of said core means, said second flexible portion being tapered along the length thereof such that essentially all of said second flexible portion can generally be extended within a coronary artery to maximize the variable stiffness of said catheter, the combination of the core means and the coated wire wound member providing variable trackability, pushability and flexibility of said catheter, said catheter including a flexible guide wire fixed and further axially extending from the second distal end of said core means, said catheter including an inflatable member having a non-inflatable sheath covering an external surface of said flexible shaft near the second distal end of said flexible shaft and further including means for inflating said inflatable member;
components in the form of an exchange wire, an angioscope, a laser fiber, a rotatable wire, and a thermal angioplasty means for thermal oblation and remodeling of tissue, all of said components sized to be insertable within said flexible shaft upon removal of said core means; and
a different balloon angioplasty catheter and a perfusion catheter, said balloon angioplasty catheter and said perfusion catheter sized to be inserted over said exchange wire.

4. A method of performing a combined fixed wire and movable wire angioplasty including the steps of:
(a) inserting a catheter in a vascular tree, said catheter including a flexible shaft having a sealed hollow passage defined therein and having a first proximal end and a second distal end, both said ends being open, said flexible shaft being a coated wire wound member, said coating being fluid impervious and extending along substantially the entire length of the wire wound member, the wire wound member being substantially round in cross-section and resistant to flattening in cross-section when said flexible shaft is bent along the length thereof in the tortuous path of a coronary artery, allowing close tolerances for a member that may be inserted therein, the coated wire wound member inherently having high column strength providing pushability while maintaining a high degree of flexibility and being resistant to a preset in overall shape when the catheter is coiled for storage, said catheter including a core means movably, removably and substantially contained within said flexible shaft, said core means having a first proximate end and a second distal end and having a first flexible portion extending from said first proximate end and a second flexible portion terminating in said second distal end of said core means, said second flexible portion being of greater flexibility than said first flexible portion, said second flexible portion having a variable core strength along the length thereof from greater to lesser strength extending toward the second distal end of said core means, said second flexible portion being tapered along the length thereof such that essentially all of said second flexible portion can generally be extended within a coronary artery to maximize the variable stiffness of said catheter, the combination of the core means and the coated wire wound member providing variable trackability, pushability and flexibility of said catheter, said catheter including a flexible guide wire fixed to and further axially extending from the second distal end of said core means, said catheter including an inflatable member having an integral non-inflatable sheath covering an external surface of said flexible shaft near the second distal end of said flexible shaft and further including means for inflating said inflatable member; and
(b) moving said second flexible portion of said core means axially relative to said second distal end of said flexible shaft, extension of the second flexible portion relative to the second distal end of said flexible shaft increasing pushability of the catheter and decreasing flexibility and trackability, retraction of said second flexible portion from such extended position increasing flexibility and trackability of the catheter with an accompanying decrease in pushability.

5. A method according to claim 4 further including the steps of:
(c) removing said core means through said first proximal end of said flexible shaft;
(d) inserting an exchange wire within said flexible shaft;
(e) removing said flexible shaft; and
(f) inserting a different balloon angioplasty catheter over said exchange wire.

6. A method according to claim 4 further including the steps of:
(c) removing said core means through said first proximal end of said flexible shaft;
(d) inserting an exchange wire within said flexible shaft;
(e) removing said flexible shaft; and
(f) inserting a perfusion catheter over said exchange wire.

7. A method according to claim 4 further including the steps of:

(c) removing said core means through said first proximal end of said flexible shaft; and
(d) inserting an angioscope within said flexible shaft.

8. A method according to claim 4 further including the steps of:
(c) removing said core means through said first proximal end of said flexible shaft; and
(d) inserting a laser fiber within said flexible shaft.

9. A method according to claim 4 further including the steps of:
(c) removing said core means through said first proximal end of said flexible shaft; and
(d) inserting a rotatable wire within said flexible shaft.

10. A method according to claim 4 further including the steps of:
(c) removing said core means through said first proximal end of said flexible shaft; and
(d) inserting within said flexible shaft a thermal angioplasty means for thermal oblation and remodeling of tissue.

* * * * *

UNITED STATES PATENT AND TRADEMARK OFFICE
CERTIFICATE OF CORRECTION

PATENT NO. : 4,927,413

DATED : May 22, 1990

INVENTOR(S) : Robert Hess

It is certified that error appears in the above-identified patent and that said Letters Patent is hereby corrected as shown below:

Column 1, line 47, delete "and" and insert therefor --end--.

Column 3, lines 66 and 67, delete "designed" and insert therefor --designated--.

Column 5, line 3, delete "fin-tuning" and insert therefor -- fine-tuning --.

Column 8, lines 8 and 9, delete "sized to fit, with respect to the catheters of the".

Column 8, line 40, following "system.", begin a new paragraph and insert --Because of the extremely low profile, this system may be inserted through conventional, diagnostic--.

Column 9, line 12, delete ")." and insert therefor --.)--.

Column 9, line 45, following "angioplasty" insert --,--, a comma.

Column 11, line 4, delete "comprising" and insert therefor --including--.

Signed and Sealed this

Third Day of September, 1991

Attest:

HARRY F. MANBECK, JR.

Attesting Officer

Commissioner of Patents and Trademarks